United States Patent [19]

Selby et al.

[11] Patent Number: 5,852,230
[45] Date of Patent: Dec. 22, 1998

[54] DEVICE TO TEST PUMPABILITY OF OILS AT LOW TEMPERATURE

[75] Inventors: Theodore W. Selby, Midland; Stephanie J. Resio, Reese; Robert H. Seer, Midland; James R. Cotter, Bay City, all of Mich.

[73] Assignee: Savant, Inc., Midland, Mich.

[21] Appl. No.: 831,561

[22] Filed: Apr. 9, 1997

[51] Int. Cl.[6] .................................................. G01N 11/14
[52] U.S. Cl. ........................................ 73/54.35; 73/54.43
[58] Field of Search ............................... 73/54.28, 54.29, 73/54.31, 54.32, 54.33, 54.34, 54.35, 54.43

[56] References Cited

U.S. PATENT DOCUMENTS

| 2,365,339 | 12/1944 | Green | 73/54.33 |
|---|---|---|---|
| 3,435,666 | 4/1969 | Fann | 73/54.39 |
| 4,648,263 | 3/1987 | Deysarkar et al. | 73/54.35 |
| 5,503,002 | 4/1996 | Selby et al. | 73/54.28 |
| 5,587,522 | 12/1996 | Selby | 73/54.28 |

OTHER PUBLICATIONS

ASTM D 4684–92, "Standard Test Method for Determination of Yield Stress and Apparent Viscosity of Engine Oils at Low Temperature," 1992.

*Primary Examiner*—Michael Brock
*Attorney, Agent, or Firm*—Christopher John Rudy

[57] ABSTRACT

Device can include an array of stators placed in a carousel which can hold the stators in the array apart from one another while precisely cooled by a suitable source. For example, the device can be provided with cooling in conjunction with an instrument having a highly circulated, cold liquid bath for temperature control such as by insertion of the stators in the carousel through housing of a versatile sensitive rotating viscometer instrument into its bath. The sample carousel has a lower base containing a plurality of stator accommodating orifices in a first array, and an upper base connected to the lower base. The upper base can have a plurality of rotor control pin accommodating orifices in a second array, and the upper base is mounted to the lower base such that the second array of orifices in the upper base is disposed in registry with the first array of orifices in the lower base. A rotor control pin serving several functions can be mounted in one of the rotor control pin accommodating orifices, which can be moved into controlling contact with a rotor inserted in a stator, and a stator can be mounted in one of the stator accommodating orifices. The first array is such that, when a plurality of stators are mounted in the stator accommodating orifices, one for each of the orifices in the first array, and the carousel is positioned in a temperature control bath having a temperature control fluid, the fluid can be circulated between any two of the mounted stators among the stators mounted in the complete array. The stator can be of a plurality of pieces, for ease of operation and cleaning, with a rotor guiding needle on a bottom cap, and the rotor can have a concave part on its bottom, for accepting the needle and a lateral rotor control part on its top. Low temperature testing of oils can be carried out with high accuracy, precision and responsiveness.

15 Claims, 6 Drawing Sheets

DEVICE TO TEST PUMPABILITY OF OILS AT LOW TEMPERATURE

FIELD

The present invention concerns a device useful in viscometric testing of fluids. In particular, it concerns a device for testing of the pumpability of engine oils at low temperatures.

BACKGROUND

The performance of engine oils and other lubricants at low temperatures is of increasing concern, and various technology has developed in order to ascertain, in advance, properties of the oils which would be determinative of likely success or failure under low temperature operating conditions, particularly at start up and cold temperature operation of motor vehicle internal combustion engines. In the testing of engine oils at low temperatures, it is critical for performance of the test that the test oil be maintained at a particular temperature and/or be controlled to have a certain rate of increase or decrease in temperature. For example, ASTM D 4684-92 covers the measurement of the yield stress and viscosity of engine oils after cooling at controlled rates over a period exceeding forty-five hours to a final test temperature of between minus fifteen and minus thirty-five degrees Celsius.

In addressing such requirements, certain devices have been provided. For example, for the aforementioned ASTM test method, a Mini-Rotary Viscometer is available from Cannon Instrument Co., State College, Pa., which is an apparatus having a number of, for example, nine, viscometric cells formed in the same temperature-controlled aluminum block. The block is typically cooled by a refrigerated liquid bath, which requires a circulating system to pump the coolant from the refrigeration device to the block and back again to the bath to cool the block. A temperature-controller in the aluminum block is employed to help in attempting to hold the temperature at the programmed set temperature.

Such technology is not without its drawbacks. Among these may be mentioned a lack of precision and accuracy. In the known device, for example, cooling of the aluminum block by the cooling fluid is along a flow path through the aluminum block, and accordingly, the block is cooler at the cooling fluid entry end than at the exit end because of temperature gain from the environment in the room; this effect is exaggerated at colder test temperatures.

A phenomenon known as oil gelation also occurs under certain low-temperature cooling conditions. This gelation phenomenon poses a considerable further difficulty in practicing the art of low temperature rheology. In practice, the ASTM D 4684-92 test method cannot reliably cause the formation of gelation nor reliably determine the degree of the presence of gelation according to the literature on the subject. For this reason, the aforementioned ASTM method cannot assign a precision value to determinations of gelation even though this is an important factor in causing engines to fail in operation.

Moreover, the design of the device used in the aforementioned ASTM method uses only one fixed test protocol which employs very slow cooling conditions down only to minus twenty degrees Celsius (and fast cooling conditions thereafter). However, it has been shown that gelation also occurs at lower temperatures, which requires slow cooling conditions below minus twenty degrees Celsius to observe as well.

Note, Selby et al., SAE Technical Paper Series No. 922287, "Problems in Bench Test Prediction of Engine Oil Performance at Low Temperature." This paper was presented at the International Fuels and Lubricants Meeting and Exposition, San Francisco, Calif., Oct. 19–22, 1992.

Furthermore, the Mini-Rotary Viscometer device design has only a limited number of test cells. These test cells cannot be removed for cleaning of the previous oil sample, and the operator must rely on vacuuming out the previous test sample as well as vacuuming of the solvents, followed by drying.

It would be desirable to overcome such problems. In particular, with engine oil testing becoming more and more important, and the need developing for higher and higher accuracy and precision therein, it would be desirable to provide improved testing technology to the art of rheology and tribology.

SUMMARY

The present invention provides a device useful for testing pumpability of an oil, which can comprise a sample carousel having a lower base containing a plurality of stator accommodating orifices in a first array; an upper base connected to the lower base, the upper base having a plurality of rotor control member accommodating orifices in a second array, wherein the upper base is mounted to the lower base such that the second array of orifices in the upper base is disposed in registry with the first array of orifices in the lower base; a rotor control member mounted in one of the rotor control member accommodating orifices, which can be moved into controlling contact with a rotor inserted in a stator; and a stator mounted in one of the stator accommodating orifices—wherein the first array is such that, when a plurality of stators are mounted in the stator accommodating orifices, one for each of the orifices in the first array, and the carousel is positioned in a temperature control bath having a temperature control fluid, the fluid can be circulated between any two of the mounted stators among the stators mounted in the complete array. Certain parts or subcombinations hereof may be featured separately from other parts and subcombinations, and additional parts or subcombinations may be featured in combination with the foregoing, and be within the practice of the present invention. For example, the unit may not have a stator and/or rotor control member present, or the unit may be mounted so as to have its stators immersed in a temperature control bath tub which may be filled with temperature control fluid.

The invention is useful in fluid, especially engine oil, testing.

Significantly, by the invention, problems in the art are ameliorated if not overcome. For example, all test cells, i.e., stators filled with test fluid, can be held at the same temperature through the spaced-apart stator array and mobility of the temperature control bath fluid, e.g., cold methanol. Test accuracy and precision, and reproducibility of test runs, are notably advanced. In addition, a significantly greater number of test samples can be prepared, and tested, both in raw numbers and in numbers of samples which can be tested over a given time. User operability is of notable concern and can attain a high degree of perfection. The device permits the testing of yield stress of an oil sample at low temperatures.

DRAWINGS

The drawings, which are not necessarily drawn to scale, form part of the specification hereof. With respect to the drawings, the following is briefly noted.

ILLUSTRATIVE DETAIL

The invention can be more fully understood by the present detail, which may be read in conjunction with the drawings. The same is to be taken in an illustrative and not necessarily limiting sense.

With particular reference to the drawings, the following is noted:

Device 1000 useful for testing pumpability of an oil in accordance with the present invention can be provided in conjunction with temperature control bath containing instrument 1 such as by insertion through housing 2 of a versatile sensitive rotating viscometer instrument according to U.S. Pat. No. 5,503,002 to Selby et al., for example, a Scanning Brookfield PlusFour (TM) instrument available from Tannas Co., Midland, Mich. Particularly as modified hereby, to be an instrument with a highly circulated, cold liquid bath for temperature control, such an instrument can provide quite exacting control of cold bath temperature. See, FIGS. 1 & 12–15.

The device 1000 includes sample carousel 100 having lower base 10 which contains a plurality of stator accommodating orifices 11 in a first array. For example, twenty-eight stator accommodating orifices 11 can be provided. The lower base 10 can be of laminate construction with upper, structurally supportive layer 12 such as of a suitably stiff, strong, solvent resistant, colorfast, scratch resistant, machineable, self-extinguishing material, optionally with fair or better passive thermal insulative properties, for example, a treated thermoplastic, e.g., ¼-inch KYDEX-100 acrylic-polyvinylchloride alloy; and with sub-layer 13 of any suitable material such as a suitably stiff and strong, usually more stiff and strong than the layer 12, solvent resistant, high moisture resistant, high temperature resistant, readily machineable material, desirably with good passive thermal insulative properties, optionally of laminate construction, for example, an oil-impregnated nylon composite, e.g., NYLATRON composite. The layer 12 can extend beyond the sub-layer 13 and provide 14 shoulder to assist in positioning the carousel 100 in a step 3 in the housing 2 of the instrument I. Thus, the carousel is supported above the bath tub 4 full of cold methanol. The orifices 11 may have stator anti-rotation key tabs 15 cut into the layer 12. The layer 12 and sub-layer 13 may be fastened together with screws 16. One or a plurality, for example, four, upper base supporting posts 17 are present and may have top threads 18. The carousel 100 holds a plurality of stators 20, one per orifice 11. Each stator 20 holds one rotor 30. See, FIGS. 1–3 & 15.

The carousel 100 also has upper base 40, which is connected to the lower base 10 through the posts 17. The upper base 40, for example, of aluminum, has a plurality of rotor control member accommodating orifices 41 in a second array, and the upper base 40 is mounted to the lower base 10 such that the second array of orifices 41 in the upper base 40 is disposed in registry with the first array of orifices 11 in the lower base 10. Accordingly, for example, twenty-eight rotor control member accommodating orifices 41 can be present. The upper base 40 may be provided in stacked or laminate fashion, for example, with top plate 42, mid-level plate 43, and bottom level plate 44. Opposing rotor control member check devices 45, one per orifice 41, can be provided in a recess in one or more of the plates, for example, in the bottom level plate 44 such as by provision of safety pins. The rotor control member check devices 45 can act as springs. The plates 42, 43, 44 may have threaded screw holes 46 and be fastened together with sets of hex head screws 46t (top) & 46b (bottom) which are threaded therein. Post holes 47 permit passage of the four posts 17. Post nuts 48 can be employed to secure the upper base 10 to the lower base 40 by threading onto the male threads 18 on the posts 17. Bronze shoulder bushings 49 may be set in the rotor control member accommodating orifices 41 of the top plate 42. See, FIGS. 1 & 4–6 & 12–14.

In the carousel 100, rotor control members 50 are mounted in the orifices 41, one control member 50 per orifice 41. The member 50 can be moved into controlling contact with a rotor 30 inserted in a stator 20, and the member 50, for example, of stainless steel, has generally elongate, cylindrical shaft 51; lateral rotor control rod 52, for example, of hardened steel, and rounded for easier insertion into the rotor, which extends from a first end of the shaft 51; blade tip 53 about the first end of the shaft 51 from which the rod 52 extends, and the blade tip 53 can have opposing concavely curved blade stem faces 54 for easier insertion into the rotor 30; drive control position groove 55 about the circumference of the shaft 51 and above the blade tip 53; index spots 56 on or in the shaft 51 above the groove 55, which index spots 56, for example, may be in the form of scooped position check gouges set at the 12-o'clock, 3-o'clock, 6-o'clock, and 9-o'clock positions around the shaft 51 above the groove 55; and knurled knob 57. The groove 55 and index spots 56 cooperate with the spring or other rotor control check member device 45 when set into position, for example, by hand with use of the knurled knob 57. The member 50 can be lowered into a position determined by the index spots 56 for set up and conditioning, and, in addition, the index spots 56 facilitate rotational position stops of the rotor 30 at 90-degree intervals. The member can be raised into a position determined by the groove 55 so that the rotor is free to rotate under lateral control of the rod 52 inserted into the rotor 30. See, FIGS. 1, 8, 9 & 12–14.

In the carousel 100 can be mounted one or more stators 20, one per stator accommodating orifice 11 of the lower base 10. Accordingly, for example, there may be twenty-eight stators 20 mounted. Preferred stator 20, for example, generally of stainless steel top components, includes the top components of upper shoulder 21, to assist in keeping the stator 20 in supported position by the sub-layer 13 in the orifice 11, which orifice 11 can have a smaller diameter through the sub-layer 13 than through the overlying layer 12; hollow, internally cylindrical housing 22, which may be externally cylindrical as well; lower, inside sealing shoulder 23; lower component accepting part 24, which may take the form of an L-shaped insert slot which can have a ramp feature about its lower boundary; and anti-rotation stop arm or post 25 about the top end of the housing 22, which can be registered with and guided into the slot 15 so as to keep the mounted stator from rotating during testing. The preferred stator 20 includes bottom sealing and rotor axis providing plug 26 for acceptance by the top component. The plug 26, for example, generally of aluminum, can include inert, resilient sealing gasket 27, for example, of a silicone rubber, to seal the housing 22 with the plug 26 when the plug is properly inserted into the housing 22 so that sealing pressure is applied to the gasket 27 from the shoulder 23 and the plug 26 so as to keep test sample, e.g., engine oil, in the stator and cooling fluid, e.g., methanol, out; bottom rotor rotating support and rotational axis providing needle 28 extending from the plug 26, and which needle 28 is upwardly directable when the top and bottom component parts are suitably mated; and sealing stop arm 29, which rides in the insert slot 24, and, with the twist of the plug 26, provides the plug 26 with sealing pressure as it rides across and slightly up the ramp of the slot 24. See, FIGS. 3, 7 & 8.

In such a stator as the stator 20 is inserted rotor 30. Preferred rotor 30 includes shaft 31, for example, of stainless steel; top, center axis hole and bearing 32, for example, of hardened steel, which may be provided as an insert mating bearing pressed into the shaft 31, and into which the rod 52 is inserted; slot 33, into which blade tip 53 is inserted for driving and stopping control of the rotor during set up of the carousel 100 and device 1000; snap ring 34, which may have special open hook 35 so that a string with a weight, used during testing in a method analogous to but advanced from and more precise and accurate than ASTM D 4684-92, can be readily attached and yet not slip off at the last turn of the rotor 30; drum 36, for example, of a polytetrafluoroethylene such as TEFLON polymer; bottom, larger orifice 37, and lower, bearing 38, for example, of hardened steel, which may be provided as an insert arrangement pressed into the shaft 31, which orifice 37 and bearing 38, respectively, guide and accept the needle 28. Although not part of the rotor 30 per se, plastic insulating cap 39 can be loosely mounted on the rotor shaft 31 before setting of the snap ring 34, and the cap 39 can be inserted into the stator 20 so as to provide insulation from warm air for the sample during conditioning and testing. See, FIGS. 1–3, 7, 8, 10 & 12–14.

In the carousel 100, the first array is such that, when a plurality of stators 20 are mounted in the stator accommodating orifices 11, one for each of the orifices in the first array, and the carousel 100 is positioned in a temperature control bath 4 having a temperature control fluid, the fluid can be highly circulated between any two of the mounted stators 20 among the stators 20 mounted in the complete array. Thus, temperature control can be highly responsive, precise and accurate. To accomplish this in a cold fluid bath such as in methanol at minus ten to minus forty degrees Celsius, where it has been found that magnetic stirring bars provide insufficient mixing, a pump 60 such as of the submersible type is provided at a suitable position to provide for high levels of circulation of cold bath liquid. Preferably, a plurality of the submersible pumps 60, for example, a set of three aquarium pumps, each a Fluval-1 model, are provided in the bath tub 4 at suitable perimeter positions, which can provide for efficient, high levels of circulation of cold bath liquid. Each pump 60 has lower intake 61 and upper discharge 62 openings. See, FIG. 15.

For test purposes, particularly in a test protocol akin to the aforementioned ASTM, string 70 is wrapped around each rotor 30, with the corresponding stator 20 containing a suitable level of test fluid. The string, during testing, is stretched over pulley 80, which is concentric with easy to read, radially visible, counting wheel 81, which is mounted on the temperature control unit housing 2. Weight 82 is attached to the end of the string to provide rotational force to the rotor 30, against which the test fluid exerts drag during active testing as the weight 82 plummets due to the force of gravity, and the counting wheel is monitored. See, FIGS. 1 & 12–14.

The carousel 100 can be turned manually to expose a test position normal thereto and in line with the pulley 80, and test monitoring with the device 1000 can be done manually. See, FIGS. 1 & 12–14. The carousel 100 and the device 1000 may be automated as well. For example, servo-motors may turn an automated carousel and even automated rotor control pins therein, and the counting wheel 81 may be monitored by a light beam passing therethrough or reflecting therefrom; automatic control also may be provided through light sensing and/or mechanical devices.

Various accessory items may be provided the carousel 100 and device 1000. For an example, crown 90 having shoulder 91 to rest on the perimeter of the upper base 40, and slits 92 to accommodate the strings 70, preferably one string 70 per slit 92, can be kept ready and set upon the carousel 100 so that the array of test samples can be set up with strings 70, and the strings 70 can be kept apart from one another and under control during sample conditioning. The crown 90 may be transparent. See, FIG. 1.

When the instrument 1 has the carousel 100 removed, an insulated plug (not illustrated) can be inserted into the opening in the housing 2. In general, the insulated plug is the size of the carousel 100.

The following example further illustrates the invention.

EXAMPLE

The device of FIGS. 1–15 was set up, its bath filled with methanol.

Figures 1, 2, 3:
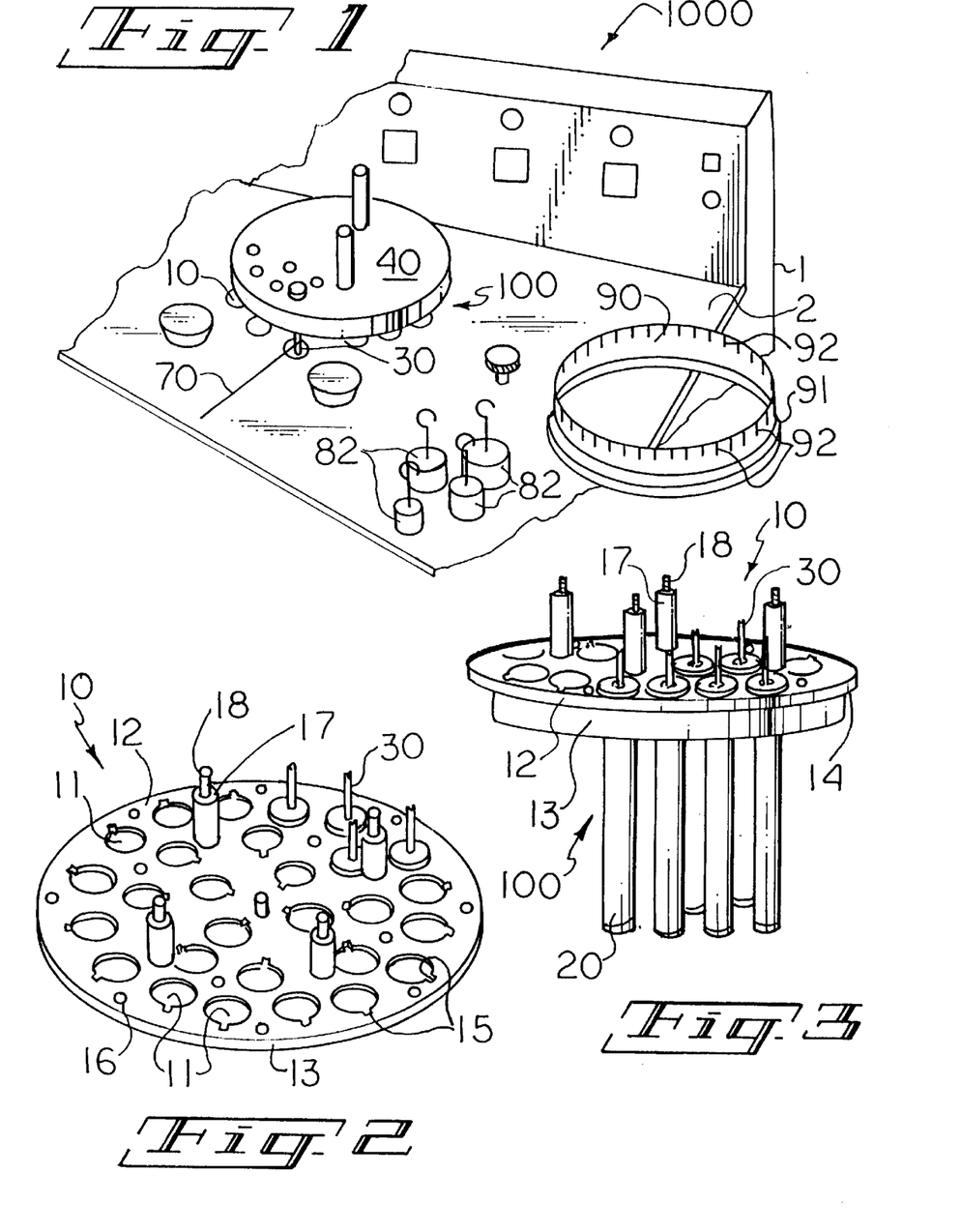
FIG. 1 is a perspective view of a device useful for testing pumpability of an oil of the present invention, with its carousel in a stage of partial completion, and with an operator preparing the same as for a sample test run on engine oil.
FIG. 2 is a top, perspective view of the carousel device depicted within FIG. 1, featuring its lower base, removed, and having a number of stator devices with rotors inserted therein.
FIG. 3 is a side, perspective view of the carousel device of FIG. 2.
Figures 4, 5, 6, 7:
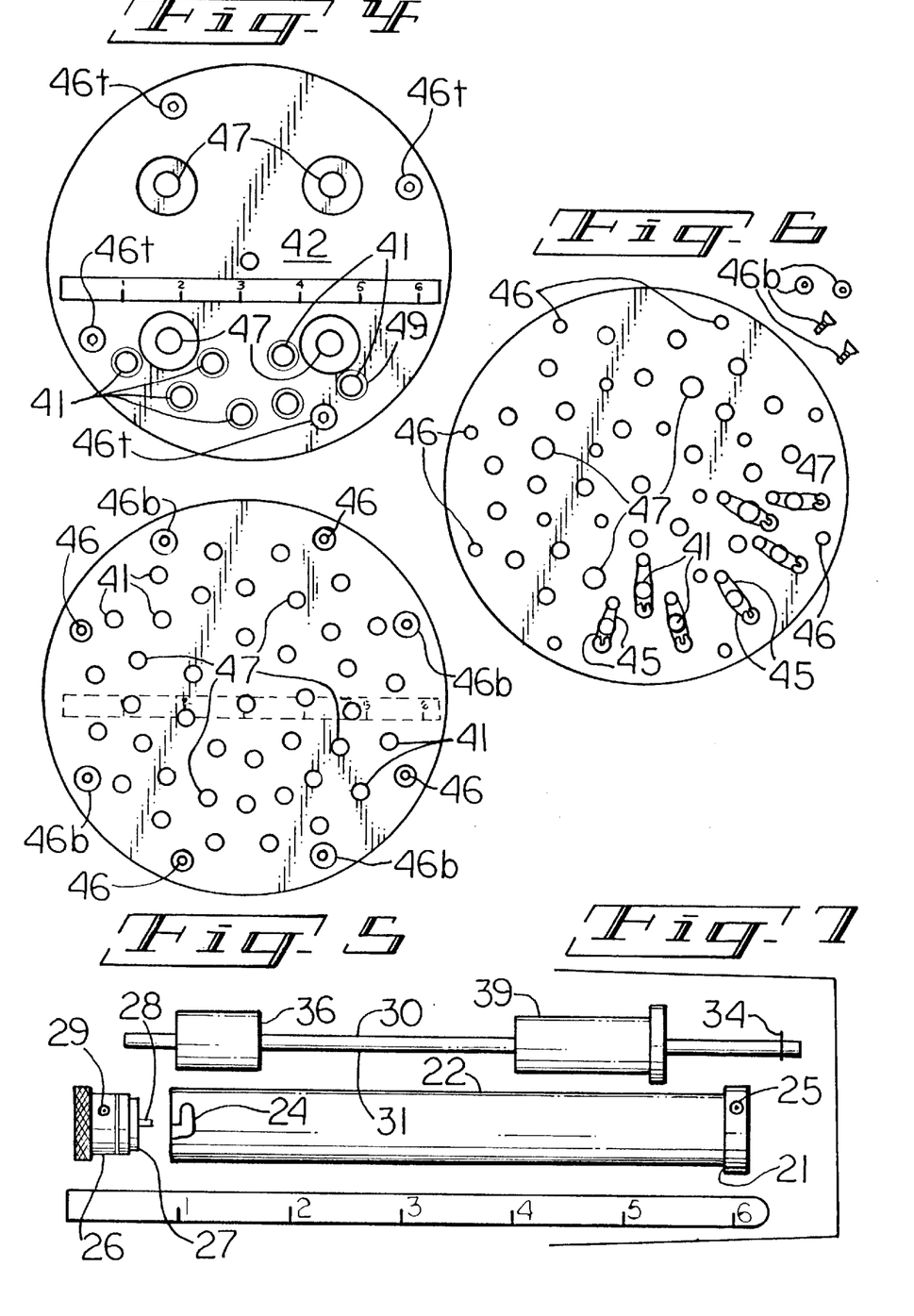
FIG. 4 is a top view of an upper base of the carousel device depicted within FIG. 1.
FIG. 5 is a top view of a mid-level plate, disassembled from the upper base top of FIG. 4.
FIG. 6 is a top view of a bottom-level plate, in a stage of partial completion, disassembled from the upper base top of FIG. 4 and the mid-level plate of FIG. 5.
FIG. 7 is an exploded, side view of component parts to a stator and a rotor, disassembled from the device of FIGS. 1–3.
Figure 8:
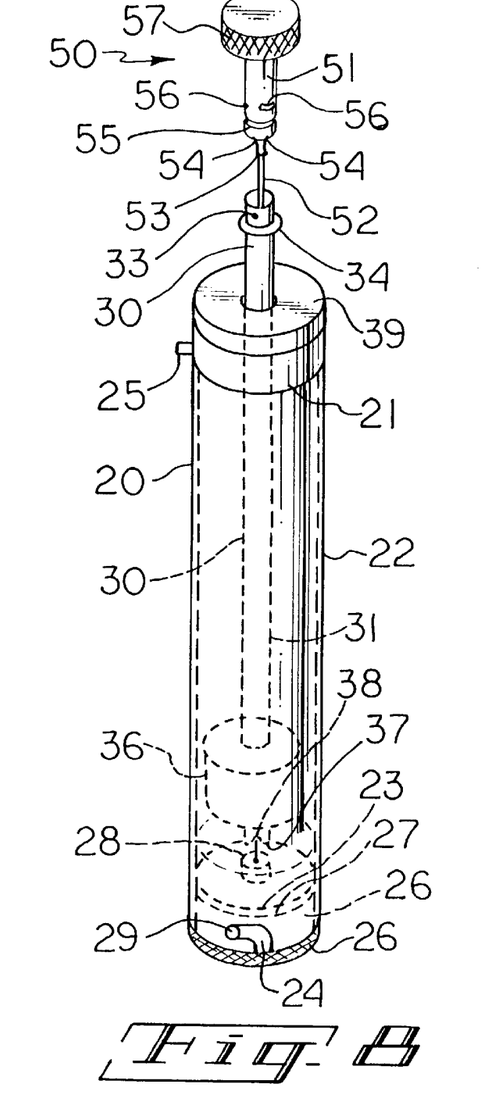
FIG. 8 is a side view, in partial section, of the component parts of FIG. 7, assembled, and showing insertion of a rotor control member by its lateral rotor control rod into the rotor shaft with rotational control elements disengaged.
Figure 9:
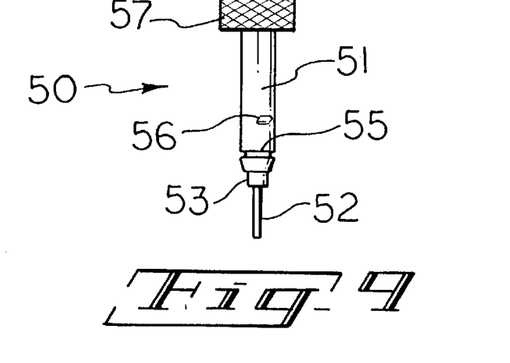
FIG. 9 is a side view of the rotor control member of FIGS. 1–3 & 8.
Figure 10:
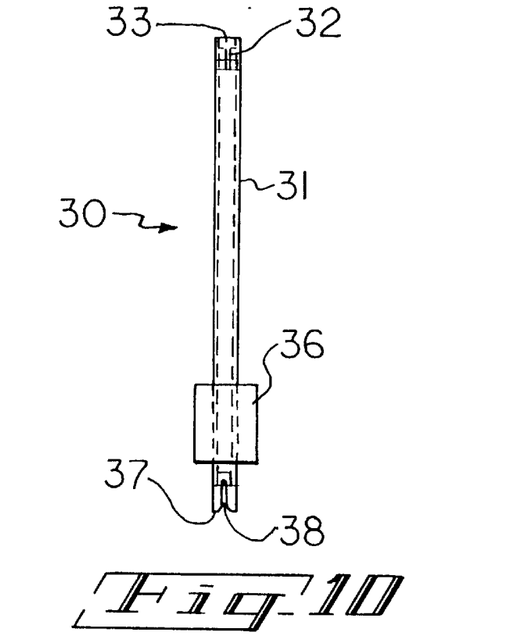
FIG. 10 is a sectional view of the rotor of FIGS. 1–3, 7 & 8.
Figure 11:
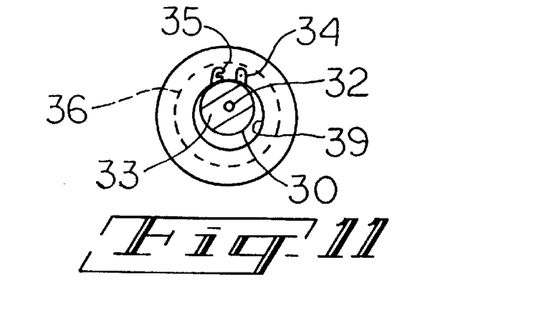
FIG. 11 is a top view of a rotor assembly having a string-hooking snap ring.
Figures 12, 13, 14:
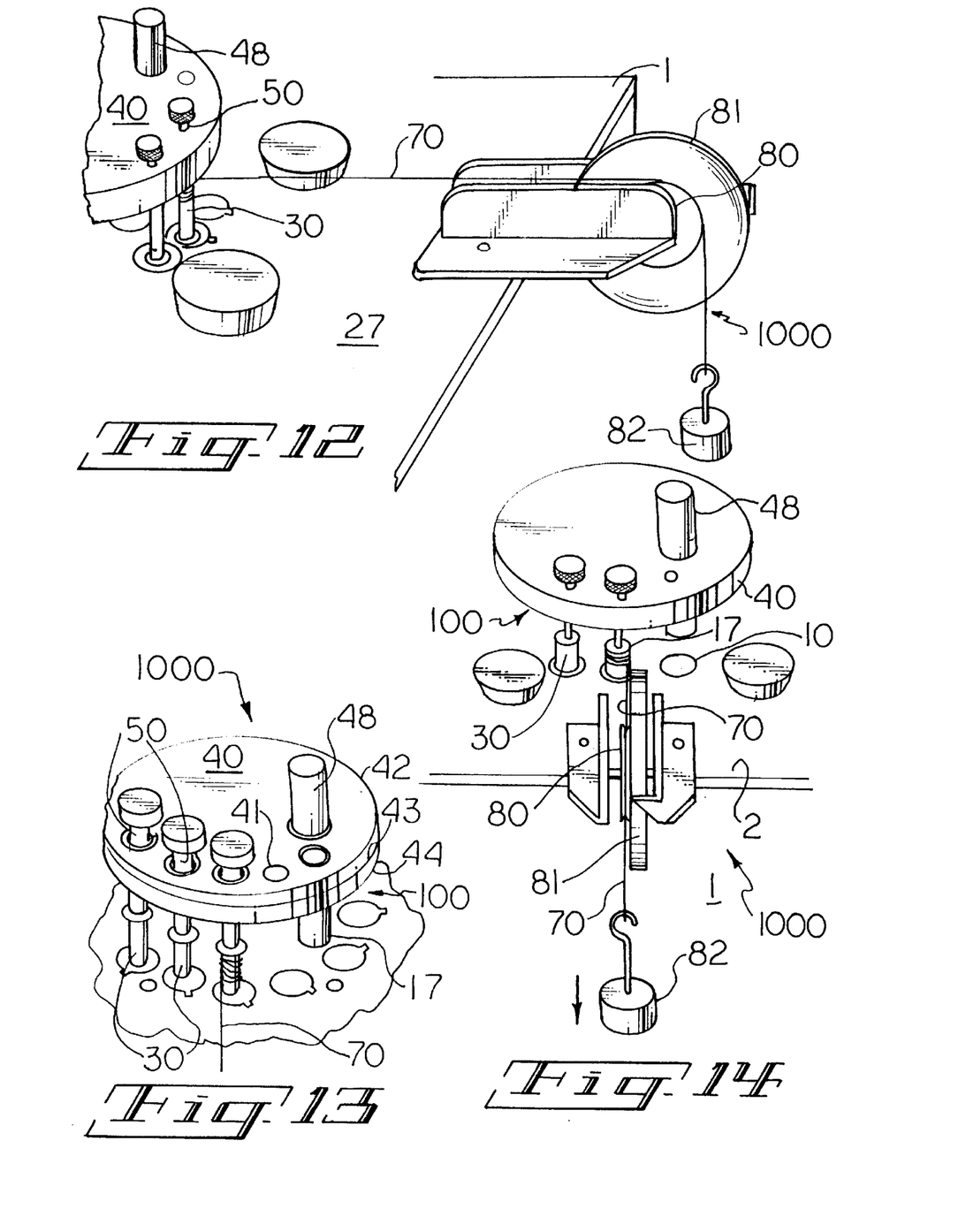
FIG. 12 is a side, perspective view of a front part of the device of FIGS. 1–11, ready to test a sample oil at cold temperature.
FIG. 13 is a front, perspective view of the device of FIGS. 1–12, with a rotor control pin being lifted so as to begin testing of the sample oil.
FIG. 14 is a front, perspective view of the device of FIGS. 1–13, during testing.
Figure 15:
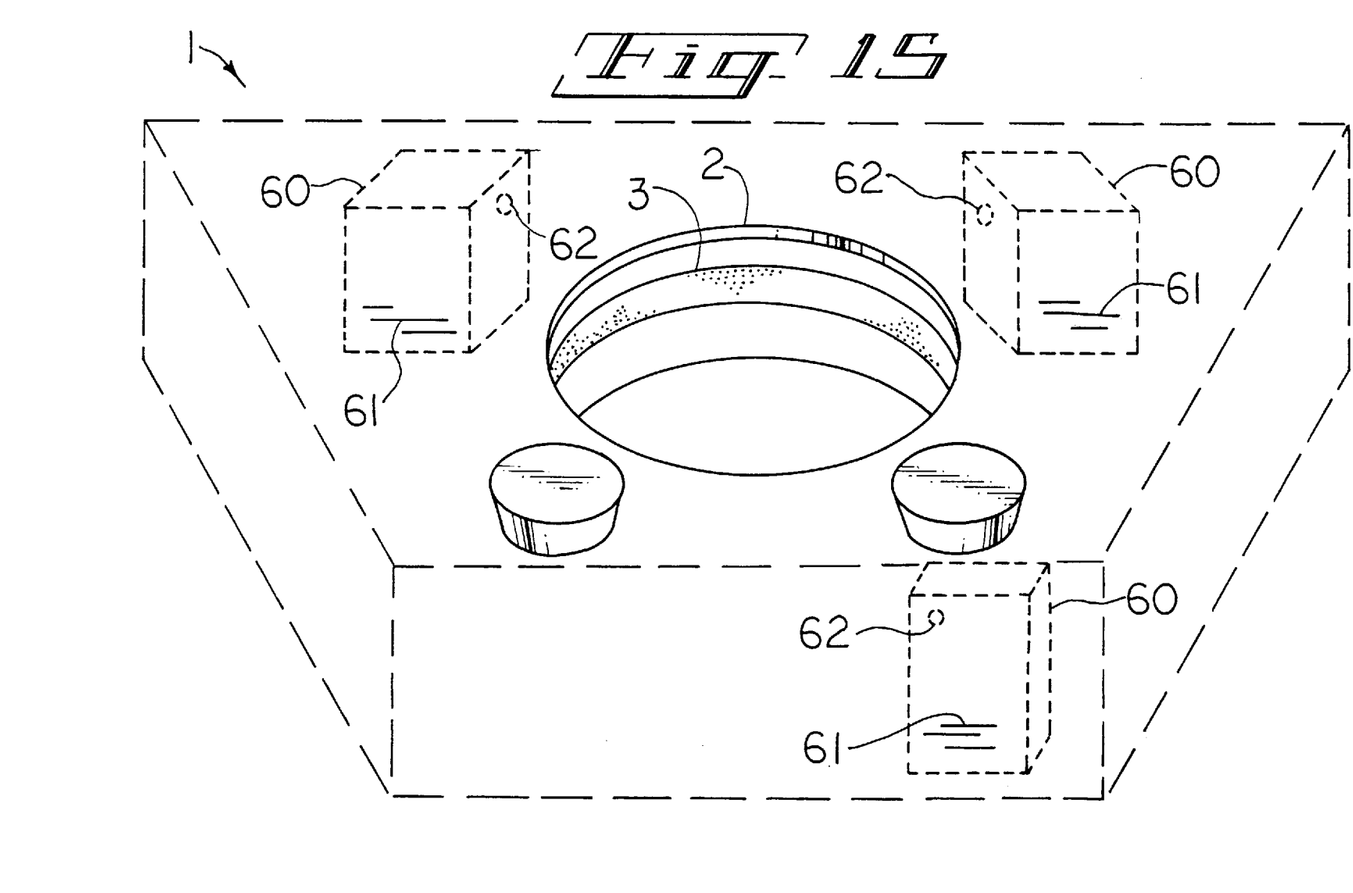
FIG. 15 is a top, perspective view, in partial section, of the temperature control fluid, tub and pump containing housing of the device of FIG. 1, open and circulating cold methanol.
Figure 16:
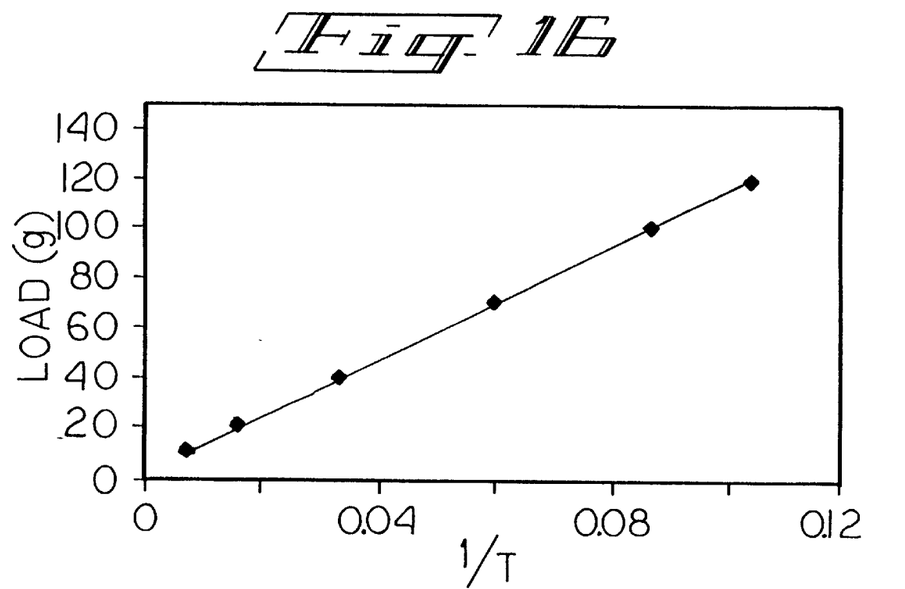
FIG. 16 is a graph of load versus reciprocal seconds (1/T) for a Newtonian fluid, obtained by employing the device of FIGS. 1–15.

Into one of its stators (cells) 20 was provided a Newtonian fluid sample. The bath methanol was held at minus twenty degrees Celsius. Obtained were the results of FIG. 16.

Figure 17:
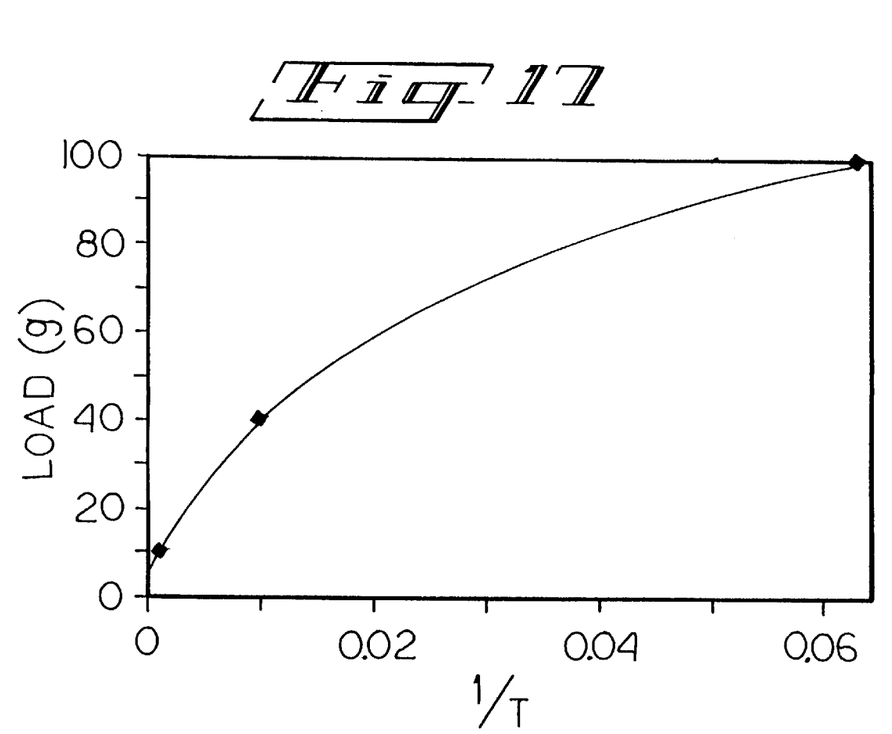
FIG. 17 is a graph of load versus reciprocal seconds (1/T) for calculation of yield stress of a non-Newtonian fluid with the device of FIGS. 1–15.

Into three of its cells 20 were provided a non-Newtonian oil sample, which was preheated to 90° to remove structural memory. The bath methanol to which the cells were placed was cooled according to ASTM D 4684-92 and held at minus twenty degrees Celsius. With the rotor 30 at rest through use of the member 50, a load 82 of ten grams was applied to the first cell to the end of the string 70; the rotor 30 was freed, and it was noted that the rotor just began to move. The rotor was stopped from rotation through use of the member 50. A second load of thirty additional (forty total) grams was applied to the second cell similarly; and the rotor stopped, then a third load of one hundred total grams was applied to the third cell similarly, and the rotor stopped. Obtained were the results of FIG. 17.

CONCLUSION

Accordingly, the device of the invention can include an array of stators placed in a carousel which can hold the stators in the array apart from one another while precisely cooled by a suitable source, and the device can be provided with cooling in conjunction with an instrument having a highly circulated, cold liquid bath for temperature control such as by insertion of the stators in the carousel through housing of a versatile sensitive rotating viscometer instrument into its bath. The sample carousel has a lower base containing a plurality of stator accommodating orifices in a first array, and an upper base connected to the lower base. The upper base can have a plurality of rotor control pin accommodating orifices in a second array, and the upper base is mounted to the lower base such that the second array of orifices in the upper base is disposed in registry with the first array of orifices in the lower base. A rotor control pin serving several functions can be mounted in one of the rotor control pin accommodating orifices, which can be moved into controlling contact with a rotor inserted in a stator, and a stator can be mounted in one of the stator accommodating orifices. The first array is such that, when a plurality of stators are mounted in the stator accommodating orifices, one for each of the orifices in the first array, and the carousel is positioned in a temperature control bath having a temperature control fluid, the fluid can be circulated between any two of the mounted stators among the stators mounted in the complete array. The stator can be of a plurality of pieces, for ease of operation and cleaning, with a rotor guiding needle on a bottom cap, and the rotor can have a concave part on its bottom, for accepting the needle and a lateral rotor control part on its top. Thus, low temperature testing of oils can be carried out with high accuracy, precision and responsiveness. Numerous further advantages attend the invention.

The present invention is thus provided. Numerous modifications can be effected within its spirit, the literal claim scope of which is particularly pointed out as follows:

We claim:

1. A device useful for testing pumpability of an oil, which comprises a sample carousel having a lower base containing a plurality of stator accommodating orifices in a first array; an upper base connected to the lower base, the upper base having a plurality of rotor control member accommodating orifices in a second array, wherein the upper base is mounted to the lower base such that the second array of orifices in the upper base is disposed in registry with the first array of orifices in the lower base; and a rotor control member mounted in one of the rotor control member accommodating orifices, which can be moved into controlling contact with a rotor inserted in a stator—wherein the first array is such that, when a plurality of stators are mounted in the stator accommodating orifices, one for each of the orifices in the first array, and the carousel is positioned in a temperature control bath having a temperature control fluid, the fluid can be circulated between any two of the mounted stators among the stators mounted in complete array.

2. The device of claim 1, further comprising at least one stator mounted in one of the stator accommodating orifices.

3. The device of claim 2, wherein a plurality of stators are mounted in the stator accommodating orifices, one stator per stator accommodating orifice.

4. The device of claim 3, which is mounted so as to have its stators immersed in a temperature control bath tub which may be filled with temperature control fluid.

5. The device of claim 4, wherein the temperature control bath tub includes a plurality of submersible pumps which can provide for high levels of circulation of cold bath liquid.

6. The device of claim 2, wherein the at least one stator comprises a stator useful in testing an oil sample at low temperature having a top component of a hollow, internally cylindrical housing; a lower, inside sealing shoulder, and a lower component accepting part; and a bottom component including a plug for acceptance by said part, and a rotor rotating support needle extending from the plug and upwardly directable when the top and bottom parts are suitably mated.

7. The device of claim 6, further comprising a rotor useful in testing an oil sample at low temperature having a shaft; a top, center axis hole and bearing; a top slot into which a blade tip can be inserted; a top snap ring; a drum mounted on the shaft; a bottom orifice and a lower bearing, which orifice and bearing, respectively, guide and accept a bottom needle of the at least one stator—said rotor being suitably mounted in the at least one stator.

8. The device of claim 1, wherein the stator accommodating orifices in the lower base have anti-rotation key tabs, and the lower and upper bases are connected by a plurality of posts.

9. The device of claim 1, having a plurality of rotor control members, one in each of the rotor control member accommodating orifices.

10. The device of claim 9, wherein the upper base is provided in laminate fashion with a plurality of plates, and opposing rotor control member check devices are provided in a recess in at least one the plates.

11. The device of claim 10, wherein the upper base includes a top plate, a mid-level plate, and bottom level plate, and the opposing rotor control member check devices act as springs.

12. The device of claim 11, wherein the opposing rotor control check member devices are provided in the bottom level plate.

13. The device of claim 9, wherein a plurality of rotor control check member devices, which act as springs, are mounted rotor control check member accommodating orifices, one rotor control check device member per check device member accommodating orifice, and one rotor control check device member accommodating orifice per rotor control member accommodating orifice.

14. The device of claim 13, wherein each rotor control member has a generally elongate, cylindrical shaft; a rotor axial position rod extending from a first end of the shaft; a blade tip about the first end of the shaft from which the rotor axial position rod extends; a drive control position groove about the circumference of the shaft and above the blade tip;

and index spots on or in the shaft above the drive control position groove.

15. The device of claim 14, wherein the rotor axial position rod is rounded at the tip; the blade has opposing concavely curved blade stem faces; the index spots are concave gouges set at the 12-o'clock, 3-o'clock, 6-o'clock, and 9-o'clock positions around the shaft; and a knob is present at an end of the shaft opposite the one end.

* * * * *